(12) United States Patent
Griffiths et al.

(10) Patent No.: US 7,674,892 B2
(45) Date of Patent: Mar. 9, 2010

(54) HSP70 FROM ARTHROBACTER

(75) Inventors: Steven Gareth Griffiths, Moncton (CA); Rachael Jane Ritchie, Fredericton (CA); Nathalie C. Simard, Fredericton (CA)

(73) Assignee: Novartis AG, Basel (CH)

( * ) Notice: Subject to any disclaimer, the term of this patent is extended or adjusted under 35 U.S.C. 154(b) by 104 days.

(21) Appl. No.: 10/521,103

(22) PCT Filed: Jul. 14, 2003

(86) PCT No.: PCT/EP03/07602

§ 371 (c)(1),
(2), (4) Date: Feb. 14, 2005

(87) PCT Pub. No.: WO2004/007539

PCT Pub. Date: Jan. 22, 2004

(65) Prior Publication Data

US 2005/0136071 A1    Jun. 23, 2005

(30) Foreign Application Priority Data

Jul. 15, 2002    (GB) ................. 0216414.3

(51) Int. Cl.
*C07H 21/04*    (2006.01)

(52) U.S. Cl. ............... 536/23.7; 536/23.4; 536/23.1; 536/24.1; 536/24.2; 435/320.1; 435/69.1; 435/69.3; 435/69.7; 435/71.1; 424/234.1; 424/827; 424/238.1

(58) Field of Classification Search ............ 536/23.7, 536/23.4, 23.1, 24.1, 24.2; 435/320.1, 69.1, 435/69.3, 69.7, 71.1; 424/234.1, 827, 238.1
See application file for complete search history.

(56) References Cited

U.S. PATENT DOCUMENTS 5,858,773 A    1/1999    Mazodier et al.

FOREIGN PATENT DOCUMENTS

| WO | WO 98 33884 | 8/1998 |
|----|-------------|--------|
| WO | WO 01 10469 | 2/2001 |
| WO | WO 01 29233 | 4/2001 |
| WO | WO 01 68865 | 9/2001 |
| WO | WO 02 04018 | 1/2002 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Murphy et al. Pediatr. Infect. Dis. J. 1989. 8: S66-S68).*
Yamanaka et al (J. Pediatrics. 1993. 122(2): 212-218.*
Newport, "Heat Shock Proteins as Vaccine Candidates", Semiars in Immunology, vol. 3, No. 1, pp. 17-24, (1991).
Gudding R. et al., "Recent Developments in fish Vaccinology", Veterinary Immunology and Immunopathology, vol. 72, pp. 203-212, (1999).
Kuzyk et al, "An Efficacious Recominant Subunit Vaccine Against the Salmonid Reckettsial Pathogen *Piscirickettsia salmonis*", Vaccine, vol. 19, No. 17-19, pp. 2337-2344, (2001).
Koch et al., "16S RDNA Studies on Members of *Arthrobacter* and *Micrococcus*: An Aid for their Futur3e Taxonomic Restructuring", FEMS Microbiology Letters, vol. 123, No. 1/2, pp. 167-171, (1994).

* cited by examiner

*Primary Examiner*—Jennifer E Graser
(74) *Attorney, Agent, or Firm*—Womble Carlyle Sandridge & Rice, PLLC

(57) ABSTRACT

The hsp70 gene from an *Arthrobacter* species has been isolated and sequenced. The encoded protein is believed to be highly immunogenic, especially in fish, and also has utility as a non-specific adjuvant, and as an adjuvanting carrier for heterologous antigens.

7 Claims, 3 Drawing Sheets

Fig. 1 SEQ ID NO:1. *Arthrobacter* hsp70 DNA sequence (5' to 3'), 2464 nt including 5' and 3' UTR. The predicted ORF (nt 291-2153) is underlined.

CTGCGAATGTCCACGTGGTGCGTGCAGTGATGCGCTTGAAGGGCATCGCACCGCGCTGAA
CCGGGTTCGACCCGGTCCCACTGAGTTCGCCAACTGAGTGGGACAAGCCCGTTCTGTCCC
AGTCACGCGGTCGACTCAGTGGGACCACGCCGCAGCGCGATCGATGGTCGCCGCACAGC
TTTTTCCAAAGTTGAGCACAGGTGGCTCAACTTAGACTTGACATTGGTCGGCTCAAGCGT
AAAGTTGATATCAGAACACTCAACTTGTAAGAAATCCCGAAAGGAAAAAACATGTCACG
TGCAGTAGGCATCGACCTCGGAACCACCAACTCGGTGGTTTCCGTCCTCGAAGGCGGCGA
GCCCGTCGTCATCGCGAACGCCGAAGGCGGCCGCACCACCCCCTCAGTCGTCGCGTTCTC
CAAGAGCGGTGAAGTCCTGGTCGGCGAAATCGCCAAGCGCCAGGCCGTCAACAACATCG
ATCGCACCATCGCCTCGGTCAAGCGCCACATGGGCACCGACTGGACCGTCGGCATCGACG
ACAAGAAGTACACCGCGCAGGAAATCTCCGCCCGCACCCTGATGAAGCTCAAGAACGAC
GCCGAGTCCTACTTGGGCGAAAAGGTCACCGACGCGGTGATCACGGTTCCTGCCTACTTC
AACGACGCCGAGCGCCAGGCCACCAAAGAAGCCGGTGAGATCGCCGGCCTGAACGTGCT
GCGCATCGTCAACGAGCCCACTGCGGCGGCGCTGGCCTATGGCTTGGACAAAGGCAAAG
AAGACGAACTCATCCTGGTCTTCGACCTCGGTGGCGGCACCTTCGACGTCTCGCTGCTGG
AAGTCGGCAAAGACGACGACGGCTTCTCCACGATCCAGGTCCGCGCCACCTCCGGCGAC
AACCGCCTGGGCGGCGACGACTGGGATCAGCGGATCGTCGACTACTTGCTGAACCAGCTC
AAGGTCAAGGGCATCGACCTCTCCAAGGACAAGATCGCGCTGCAGCGTCTGCGCGAAGC
TTCCGAGCAGGCCAAGAAGGAACTCTCCTCGGCCACCAGCACCAACATCTCGCTGCAGTA
CCTCTCGGTCACCCCTGACGGTCCGGTGCACTTGGACGAGCAGCTGACCCGGGCGAAGTT
CCAGGAACTGACCGCTGATCTGCTCGAGCGCACCAAGAAGCCGTTCCAGGACGTGATCGC
CGAGGCCGGGATCAAGGTTTCCGACATCGACCACATCGTGCTGGTCGGCGGTTCCACCCG
GATGCCCGCAGTGACCGAATTGGTCAAGCAGCTGGCCGGTGGCAAGGAGCCGAACAAGG
GCGTCAACCCGGACGAGGTGGTCGCCGTCGGCGCCGCGCTGCAAGCCGGCGTGCTCAAG
GGCGAACGCAAAGACGTGCTGCTCATCGACGTCACCCCGCTTTCCCTCGGCATCGAAACC
AAGGGCGGCGTGATGACCAAGCTGATCGAGCGGAACACCGCGATTCCGACCAAGCGGTC
CGAGACCTTCACCACGGCGGACGACAACCAGCCTTCGGTGGCCATCCAGGTGTTCCAAGG
CGAGCGCGAGTTCACCCGGGACAACAAGCCGTTGGGCACCTTCGAACTGACCGGCATCG
CACCGGCTCCGCGCGGCGTGCCGCAGGTCGAAGTCACCTTCGACATCGACGCCAACGGCA
TCGTGCACGTGTCGGCCAAAGACAAGGGCACCGGCAAGGAGCAGTCGATGACCATCACC

Fig. 1 continued

GGCGGTTCCTCGCTGTCCAAGGAAGACATCGAGCGCATGGTCGCCGACGCCGAGGCACA
CGCTGCAGAGGACAAGGCCCGGCGCGAGCAGGCCGAGGCCCGCAACAGCGCCGAGCAGC
TGGCGTACTCGGTGGACAAGATCCTCACCGACAATGACGACAAGCTGCCGGAAGAGGTC
AAGACGGAGGTCAAGGCCGACGTCGGGGCGCTCAAGACCGCGCTGGCCGGCACCGATGA
GGACGCGGTCGAGGCGGCCTCGGAGAAGCTGCAGGCTTCGCAGACCAAACTCGGCGGAG
CGATTTACGCTTCGGCCCAGGCCGAGGGTGCCGCCGCTGCCGGTGACGCCCCGAGCGAAG
GTGCCAAGCCCGACGAAGACATCGTCGACGCCGAGATCGTGGACGAAGAAGAACCGAAG
AACGAGAAGAAGTAGTCATGTCCGACCAGAGCCAATCTGATCAGGGCCGCAACCCCGAA
AAAGACGAAACCGACGTGGACCCGGCAACGGGTCCCGCCGGGGACGTTCCGGAGGAGCA
GGATCCTTTGGCGCAAGTCGAAGACATCCTGAACAATGCCGAGGTGCCCGCCGACGAGTC
GGTGGCCCAGGGCGCCGGGCAGGTGGATGCCGCAGAACTCAAGAACGATCTGCTGCGCT
TGCAGGCCGAATACGTGAACTACCGCAAACGCGTCGAGCGGGACACCAGCCCGGGCCGT
CGACCACGCGTGCCCTATAGTAAGGGC

Fig.2 SEQ ID NO: 2. Predicted amino acid sequence of *Arthrobacter* hsp70

MSRAVGIDLGTTNSVVSVLEGGEPVVIANAEGGRTTPSVVAFSKSGEVLVGEIAKRQAVNNI
DRTIASVKRHMGTDWTVGIDDKKYTAQEISARTLMKLKNDAESYLGEKVTDAVITVPAYFND
AERQATKEAGEIAGLNVLRIVNEPTAAALAYGLDKGKEDELILVFDLGGGTFDVSLLEVGKDD
DGFSTIQVRATSGDNRLGGDDWDQRIVDYLLNQLKVKGIDLSKDKIALQRLREASEQAKKEL
SSATSTNISLQYLSVTPDGPVHLDEQLTRAKFQELTADLLERTKKPFQDVIAEAGIKVSDIDHI
VLVGGSTRMPAVTELVKQLAGGKEPNKGVNPDEVVAVGAALQAGVLKGERKDVLLIDVTPL
SLGIETKGGVMTKLIERNTAIPTKRSETFTTADDNQPSVAIQVFQGEREFTRDNKPLGTFELT
GIAPAPRGVPQVEVTFDIDANGIVHVSAKDKGTGKEQSMTITGGSSLSKEDIERMVADAEAH
AAEDKARREQAEARNSAEQLAYSVDKILTDNDDKLPEEVKTEVKADVGALKTALAGTDEDA
VEAASEKLQASQTKLGGAIYASAQAEGAAAAGDAPSEGAKPDEDIVDAEIVDEEEPKNEKK predicted pI= 4.70 / predicted size= 66 kDa

SEQUENCE LISTING

```
<160> NUMBER OF SEQ ID NOS: 7

<210> SEQ ID NO 1
<211> LENGTH: 2464
<212> TYPE: DNA
<213> ORGANISM: Arthrobacter

<400> SEQUENCE: 1
ctgcgaatgt ccacgtggtg cgtgcagtga tgcgcttgaa gggcatcgca ccgcgctgaa      60
ccgggttcga cccggtccca ctgagttcgc caactgagtg ggacaagccc gttctgtccc     120
agtcacgcgg tcgactcagt gggaccacgc cgcagcgcga tcgatggtcg ccgcacagct     180
ttttccaaag ttgagcacag gtggctcaac ttagacttga cattggtcgg ctcaagcgta     240
aagttgatat cagaacactc aacttgtaag aaatcccgaa aggaaaaaac atgtcacgtg     300
cagtaggcat cgacctcgga accaccaact cggtggtttc cgtcctcgaa ggcggcgagc     360
ccgtcgtcat cgcgaacgcc gaaggcggcc gcaccacccc ctcagtcgtc gcgttctcca     420
agagcggtga agtcctggtc ggcgaaatcg ccaagcgcca ggccgtcaac aacatcgatc     480
gcaccatcgc ctcggtcaag cgccacatgg cgaccgactg accgtcggc atcgacgaca      540 agaagtacac cgcgcaggaa atctccgccc gcaccctgat gaagctcaag aacgacgccg     600
agtcctactt gggcgaaaag gtcaccgacg cggtgatcac ggttcctgcc tacttcaacg     660
acgccgagcg ccaggccacc aaagaagccg gtgagatcgc cggcctgaac gtgctgcgca     720
tcgtcaacga gcccactgcg gcggcgctgg cctatggctt ggacaaaggc aagaagacg      780 aactcatcct ggtcttcgac ctcggtggcg gcaccttcga cgtctcgctg ctggaagtcg     840
gcaaagacga cgacggcttc tccacgatcc aggtccgcgc cacctccggc gacaaccgcc     900
```

-continued

```
tgggcggcga cgactgggat cagcggatcg tcgactactt gctgaaccag ctcaaggtca    960
agggcatcga cctctccaag gacaagatcg cgctgcagcg tctgcgcgaa gcttccgagc   1020
aggccaagaa ggaactctcc tcggccacca gcaccaacat ctcgctgcag tacctctcgg   1080
tcacccctga cggtccggtg cacttggacg agcagctgac ccgggcgaag ttccaggaac   1140
tgaccgctga tctgctcgag cgcaccaaga agccgttcca ggacgtgatc gccgaggccg   1200
ggatcaaggt ttccgacatc gaccacatcg tgctggtcgg cggttccacc cggatgcccg   1260
cagtgaccga attggtcaag cagctggccg gtggcaagga gccgaacaag ggcgtcaacc   1320
cggacgaggt ggtcgccgtc ggcgccgcgc tgcaagccgg cgtgctcaag ggcgaacgca   1380
aagacgtgct gctcatcgac gtcaccccgc tttccctcgg catcgaaacc aagggcggcg   1440
tgatgaccaa gctgatcgag cggaacaccg cgattccgac caagcggtcc gagaccttca   1500
ccacggcgga cgacaaccag ccttcggtgg ccatccaggt gttccaaggc gagcgcgagt   1560
tcaccccggga caacaagccg ttgggcacct tcgaactgac cggcatcgca ccggctccgc   1620
gcggcgtgcc gcaggtcgaa gtcaccttcg acatcgacgc caacggcatc gtgcacgtgt   1680
cggccaaaga caagggcacc ggcaaggagc agtcgatgac catcaccggc ggttcctcgc   1740
tgtccaagga agacatcgag cgcatggtcg ccgacgccga ggcacacgct gcagaggaca   1800
aggcccggcg cgagcaggcc gaggcccgca cagcgccga gcagctggcg tactcggtgg   1860
acaagatcct caccgacaat gacgacaagc tgccggaaga ggtcaagacg gaggtcaagg   1920
ccgacgtcgg ggcgctcaag accgcgctgg ccggcaccga tgaggacgcg gtcgaggcgg   1980
cctcggagaa gctgcaggct tcgcagacca aactcggcgg agcgatttac gcttcggccc   2040
aggccgaggt gccgccgct gccggtgacg ccccgagcga aggtgccaag cccgacgaag   2100
acatcgtcga cgccgagatc gtggacgaag aagaaccgaa gaacgagaag aagtagtcat   2160
gtccgaccag agccaatctg atcagggccg caaccccgaa aaagacgaaa ccgacgtgga   2220
cccggcaacg ggtcccgccg gggacgttcc ggaggagcag gatcctttgg cgcaagtcga   2280
agacatcctg aacaatgccg aggtgccccg cgacgagtcg gtggcccagg cgccgggca   2340
ggtggatgcc gcagaactca gaacgatct gctgcgcttg caggccgaat acgtgaacta   2400
ccgcaaacgc gtcgagcggg acaccagccc gggccgtcga ccacgcgtgc cctatagtaa   2460
gggc                                                                2464
```

<210> SEQ ID NO 2
<211> LENGTH: 621
<212> TYPE: PRT
<213> ORGANISM: Arthrobacter

<400> SEQUENCE: 2

```
Met Ser Arg Ala Val Gly Ile Asp Leu Gly Thr Thr Asn Ser Val Val
  1               5                  10                  15

Ser Val Leu Glu Gly Gly Glu Pro Val Val Ile Ala Asn Ala Glu Gly
             20                  25                  30

Gly Arg Thr Thr Pro Ser Val Val Ala Phe Ser Lys Ser Gly Glu Val
         35                  40                  45

Leu Val Gly Glu Ile Ala Lys Arg Gln Ala Val Asn Asn Ile Asp Arg
     50                  55                  60

Thr Ile Ala Ser Val Lys Arg His Met Gly Thr Asp Trp Thr Val Gly
 65                  70                  75                  80

Ile Asp Asp Lys Lys Tyr Thr Ala Gln Glu Ile Ser Ala Arg Thr Leu
                 85                  90                  95
```

-continued

```
Met Lys Leu Lys Asn Asp Ala Glu Ser Tyr Leu Gly Glu Lys Val Thr
            100                 105                 110

Asp Ala Val Ile Thr Val Pro Ala Tyr Phe Asn Asp Ala Glu Arg Gln
        115                 120                 125

Ala Thr Lys Glu Ala Gly Glu Ile Ala Gly Leu Asn Val Leu Arg Ile
    130                 135                 140

Val Asn Glu Pro Thr Ala Ala Leu Ala Tyr Gly Leu Asp Lys Gly
145                 150                 155                 160

Lys Glu Asp Glu Leu Ile Leu Val Phe Asp Leu Gly Gly Gly Thr Phe
                165                 170                 175

Asp Val Ser Leu Leu Glu Val Gly Lys Asp Asp Gly Phe Ser Thr
            180                 185                 190

Ile Gln Val Arg Ala Thr Ser Gly Asp Asn Arg Leu Gly Gly Asp Asp
        195                 200                 205

Trp Asp Gln Arg Ile Val Asp Tyr Leu Leu Asn Gln Leu Lys Val Lys
    210                 215                 220

Gly Ile Asp Leu Ser Lys Asp Lys Ile Ala Leu Gln Arg Leu Arg Glu
225                 230                 235                 240

Ala Ser Glu Gln Ala Lys Lys Glu Leu Ser Ser Ala Thr Ser Thr Asn
                245                 250                 255

Ile Ser Leu Gln Tyr Leu Ser Val Thr Pro Asp Gly Pro Val His Leu
            260                 265                 270

Asp Glu Gln Leu Thr Arg Ala Lys Phe Gln Glu Leu Thr Ala Asp Leu
        275                 280                 285

Leu Glu Arg Thr Lys Lys Pro Phe Gln Asp Val Ile Ala Glu Ala Gly
    290                 295                 300

Ile Lys Val Ser Asp Ile Asp His Ile Val Leu Val Gly Gly Ser Thr
305                 310                 315                 320

Arg Met Pro Ala Val Thr Glu Leu Val Lys Gln Leu Ala Gly Gly Lys
                325                 330                 335

Glu Pro Asn Lys Gly Val Asn Pro Asp Glu Val Val Ala Val Gly Ala
            340                 345                 350

Ala Leu Gln Ala Gly Val Leu Lys Gly Glu Arg Lys Asp Val Leu Leu
        355                 360                 365

Ile Asp Val Thr Pro Leu Ser Leu Gly Ile Glu Thr Lys Gly Gly Val
    370                 375                 380

Met Thr Lys Leu Ile Glu Arg Asn Thr Ala Ile Pro Thr Lys Arg Ser
385                 390                 395                 400

Glu Thr Phe Thr Thr Ala Asp Asp Asn Gln Pro Ser Val Ala Ile Gln
                405                 410                 415

Val Phe Gln Gly Glu Arg Glu Phe Thr Arg Asp Asn Lys Pro Leu Gly
            420                 425                 430

Thr Phe Glu Leu Thr Gly Ile Ala Pro Ala Pro Arg Gly Val Pro Gln
        435                 440                 445

Val Glu Val Thr Phe Asp Ile Asp Ala Asn Gly Ile Val His Val Ser
    450                 455                 460

Ala Lys Asp Lys Gly Thr Gly Lys Glu Gln Ser Met Thr Ile Thr Gly
465                 470                 475                 480

Gly Ser Ser Leu Ser Lys Glu Asp Ile Glu Arg Met Val Ala Asp Ala
                485                 490                 495

Glu Ala His Ala Ala Glu Asp Lys Ala Arg Arg Glu Gln Ala Glu Ala
            500                 505                 510
```

```
Arg Asn Ser Ala Glu Gln Leu Ala Tyr Ser Val Asp Lys Ile Leu Thr
        515                 520                 525

Asp Asn Asp Asp Lys Leu Pro Glu Glu Val Lys Thr Glu Val Lys Ala
        530                 535                 540

Asp Val Gly Ala Leu Lys Thr Ala Leu Ala Gly Thr Asp Glu Asp Ala
545                 550                 555                 560

Val Glu Ala Ala Ser Glu Lys Leu Gln Ala Ser Gln Thr Lys Leu Gly
                565                 570                 575

Gly Ala Ile Tyr Ala Ser Ala Gln Ala Glu Gly Ala Ala Ala Ala Gly
            580                 585                 590

Asp Ala Pro Ser Glu Gly Ala Lys Pro Asp Glu Asp Ile Val Asp Ala
        595                 600                 605

Glu Ile Val Asp Glu Glu Glu Pro Lys Asn Glu Lys Lys
        610                 615                 620

<210> SEQ ID NO 3
<211> LENGTH: 20
<212> TYPE: PRT
<213> ORGANISM: Arthrobacter

<400> SEQUENCE: 3

Met Ser Arg Ala Val Gly Ile Asp Leu Gly Thr Thr Asn Ser Val Val
 1               5                  10                  15

Ser Val Leu Glu
            20

<210> SEQ ID NO 4
<211> LENGTH: 20
<212> TYPE: DNA
<213> ORGANISM: Artificial Sequence
<220> FEATURE:
<223> OTHER INFORMATION: degenerate primers for cloning Arthrobacter
      hsp70
<220> FEATURE:
<221> NAME/KEY: misc_feature
<222> LOCATION: 6, 18
<223> OTHER INFORMATION: n = A,T,C or G
<220> FEATURE:
<221> NAME/KEY: misc_feature
<222> LOCATION: 15
<223> OTHER INFORMATION: v= A, G, or C

<400> SEQUENCE: 4
gtcggnatcg acctvggnac                                              20

<210> SEQ ID NO 5
<211> LENGTH: 17
<212> TYPE: DNA
<213> ORGANISM: Artificial Sequence
<220> FEATURE:
<223> OTHER INFORMATION: degenerate primers for cloning Arthrobacter
      hsp70
<220> FEATURE:
<221> NAME/KEY: misc_feature
<222> LOCATION: 6
<223> OTHER INFORMATION: s = C or G

<400> SEQUENCE: 5
gcggtsggct cgttgac                                                 17

<210> SEQ ID NO 6
<211> LENGTH: 20
<212> TYPE: DNA
<213> ORGANISM: Artificial Sequence
```

-continued

```
<220> FEATURE:
<223> OTHER INFORMATION: degenerate primers for cloning Arthrobacter
      hsp70
<220> FEATURE:
<221> NAME/KEY: misc_feature
<222> LOCATION: 6, 9, 18
<223> OTHER INFORMATION: n = A,T,C or G
<220> FEATURE:
<221> NAME/KEY: misc_feature
<222> LOCATION: 3, 12
<223> OTHER INFORMATION: r = A or G
<220> FEATURE:
<221> NAME/KEY: misc_feature
<222> LOCATION: 15
<223> OTHER INFORMATION: y = C or T

<400> SEQUENCE: 6
cargcncana argaygcngg                                                   20

<210> SEQ ID NO 7
<211> LENGTH: 20
<212> TYPE: DNA
<213> ORGANISM: Artificial Sequence
<220> FEATURE:
<223> OTHER INFORMATION: degenerate primers for cloning Arthrobacter
      hsp70
<220> FEATURE:
<221> NAME/KEY: misc_feature
<222> LOCATION: 3, 6, 15
<223> OTHER INFORMATION: n = A,T,C or G
<220> FEATURE:
<221> NAME/KEY: misc_feature
<222> LOCATION: 9
<223> OTHER INFORMATION: y = C or T
<220> FEATURE:
<221> NAME/KEY: misc_feature
<222> LOCATION: 12, 18
<223> OTHER INFORMATION: r = A or G

<400> SEQUENCE: 7
gcncangcyt crtcnggrtt                                                   20
```

US 7,674,892 B2

HSP70 FROM *ARTHROBACTER*

This application is a National Phase Application under §371 of International Application Number PCT/EP03/07602 filed on Jul. 14, 2003.

The present invention relates to heat shock protein (hsp) genes and encoded proteins from Corynebacteria. In particular, it concerns the isolated DNA sequence and amino acid sequence of hsp70 from the genus *Arthrobacter*, and sequences homologous thereto. Further, the invention relates to varied uses of *Arthrobacter* hsp70: in the preparation of vaccines, especially vaccines for fish; as an adjuvant; and as a carrier for antigens.

BACKGROUND OF THE INVENTION

A successful vaccine against intracellular pathogens will not only stimulate the humoral immune response via the Major Histocompatibility Complex (MHC) class II pathway, but (more importantly) will also induce destruction of infected cells through activation of the MHC class I pathway. The latter response is achieved through cytosolic degradation of foreign protein in infected cells, such that fragments of the foreign material are shuttled to the cell surface for presentation to $CD8^+$ cytotoxic T cells (CTL). Failure to activate the MHC class I pathway is a common deficiency of vaccines based on purified recombinant antigens.

Heat shock proteins ("Hsps") are a family of molecular chaperone proteins produced by prokaryotic and eukaryotic cells, and which play essential roles in a multitude of intra- and intercellular processes, in particular in antigen processing and presentation of antigen fragments to the MHC I system at the cell surface. Fusion proteins of certain hsp proteins with other peptides have been successfully used in vivo to elicit a CTL response specific to those peptides.

Furthermore, hsps are now known to be targets of anti-pathogen Immune responses against a multitude of bacterial, fungal, helmintic and protozoan diseases. Immunization of mammals with a variety of different pathogen hsps (principally of mycobacterial origin) induces strong immune responses and provides protection against diseases caused by these pathogens. The strength of mammalian immune responses to pathogenic hsps is speculated to be due in part to the existence of multiple B cell and T cell epitopes on these proteins.

A live, non-virulent strain of *Arthrobacter* (a member of the family of Corynebacteria) is marketed as a vaccine intended to protect salmon and other farmed fish against bacterial kidney disease (BKD). The characteristics of this strain are disclosed in WO 98/33884. This vaccine is unique in that it is the first live culture to have been licensed for use in aquaculture.

Surprisingly, it has now been shown that *Arthrobacter* hsp70 can be effectively employed in vaccines against varied fish pathogens.

SUMMARY OF THE INVENTION

In a first aspect, the invention provides an isolated nucleic acid sequence comprising the sequence of the *Arthrobacter* hsp70 gene, a fragment thereof, or a related sequence. The gene includes the ORF, 5'UTR and 3'UTR, and any component promoter, enhancer, regulatory, terminator and localization elements.

In a second aspect the invention provides an isolated amino acid sequence comprising the sequence of the *Arthrobacter* hsp70 protein, an immunogenic fragment thereof, or a related protein.

In another aspect, the invention provides a vaccine composition comprising: a nucleic acid sequence encoding *Arthrobacter* hsp70 protein, or *Arthrobacter* hsp70 protein, or an *Arthrobacter* cell extract enriched in hsp70. The vaccine composition can be used in the preparation of a medicament for human or veterinary use, including use in aquaculture.

In a further aspect of the invention there is provided a nucleic acid sequence encoding a fusion protein of whole or part of the hsp70 protein of *Arthrobacter* with a heterologous polypeptide. Also provided is the fusion protein itself.

In yet another aspect of the Invention there is provided an entity comprising a polypeptide comprising whole or part of the hsp70 protein of *Arthrobacter*, which is covalently or non-covalently attached to a heterologous molecule.

In a further aspect of the invention there is provided use of *Arthrobacter* hsp70 protein or nucleic acid sequence as a vaccine antigen, as an adjuvant, or as a carrier for heterologous molecules, with the aim of treating or preventing animal diseases.

In a further aspect there is provided a method of inducing or enhancing an immune response to an immunogen or a hapten in an animal, the method comprising administering to said animal a pharmaceutical composition comprising a hsp70 amino acid sequence according to the invention which is covalently or non-covalently linked to a heterologous molecule, wherein the heterologous molecule comprises said immunogen or hapten.

In another aspect the invention provides a method of therapeutic or prophylactic treatment of infectious disease in a fish, comprising administering to said fish a treatment composition comprising a hsp70 nucleic acid sequence or amino acid sequence according to the invention.

In another aspect of the invention there is provided use of the *Arthrobacter* hsp70 promoter to drive expression of a heterologous gene.

In a further aspect of the invention there is provided use of an isolated heat shock protein or a nucleic acid molecule encoding a heat shock protein in the manufacture of a vaccine composition for immunizing fish against pathogenic disease; alternatively, a method for preventing or treating pathogenic disease in a fish, comprising administering to said fish a composition comprising an isolated heat shock protein or a nucleic acid molecule encoding a heat shock protein. The isolated heat shock protein is preferably a hsp70 from a bacterial source, such as *Arthrobacter*.

DESCRIPTION OF THE FIGURES

FIG. 1 depicts SEQ ID NO:1, i.e. the DNA sequence (5' to 3') of the hsp70 gene isolated from *Arthrobacter* ATCC 55921, including 5' and 3' UTR sequences.

FIG. 2 shows SEQ ID NO:2, i.e. the amino acid sequence predicted to be encoded by the hsp70 gene sequence of FIG. 1.

DETAILED DESCRIPTION OF THE INVENTION

The novel sequences of the isolated hsp70 gene of the invention and the encoded isolated or purified protein are provided in FIGS. 1 and 2, respectively. The invention encompasses nucleic acid sequences and amino acid sequences which are substantially homologous to the sequences provided in the Figures. "Substantially homologous" means that a sequence, when compared to a reference sequence, has at least 60% homology, preferably at least 70% homology, more preferably at least 80%, 85%, 90%, 95%, 98% or greater homology to the reference sequence.

To determine the percent homology of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence and the intervening non-homologous sequence in the gap can be disregarded for comparison purposes). There is no requirement for the two sequences to be the same length. Unless otherwise specified, the length of sequence across which the sequences are compared is the entire extent of the alignment. Optionally, the length of a reference sequence aligned for comparison purpose is at least 30%, preferably at least 40%, more preferably at least 50%, even more preferably at least 60%, and even more preferably at least, 70%, 80%, or 90% of the length of the reference sequence. It possible to restrict homology analysis to any particular portion of the reference sequence, e.g. in the case of hsp70 one might wish to restrict the reference sequence to the amino terminal half of the gene or protein, or more specifically to structural lobe II (Flaherty et al. (1990) Nature 346: 623-628 & Zhu et al. (1996) Science 272: 1606-1614).

When a position in the first (reference) sequence is occupied by the same amino acid residue or nucleotide as the corresponding position in the sequence, the molecules are homologous at that position (i.e. there is identity at that position). In the case of nucleic acid sequence comparison there is also homology at a certain position where the codon triplet including the nucleotide encodes the same amino acid in both molecules being compared, due to degeneracy of the genetic code.

The percent homology between two sequences is a function of the number of homologous positions shared by the sequences (i.e., % homology=no. of homologous positions/total no. of positions). Optionally, the comparison of sequences and determination of percent homology can be accomplished using a mathematical algorithm. Suitable algorithms are incorporated in to the NBLAST and XBLAST programs of Altschul et al. (1990) J. Mol. Biol. 215:430-10.

Also comprised within the nucleic acid sequences of the invention are sequences which hybridize to the reference SEQ ID NO:1 under stringent conditions. "Stringent" hybridization conditions in the sense of the present invention are defined as those described by Sambrook et al., Molecular Cloning, A Laboratory Manual, Cold Spring Harbor Laboratory Press (1989), 1.101-1.104, i.e. a positive hybridization signal is still observed after washing for 1 hour with 1×SSC buffer and 0.1% SDS at 55° C., preferably at 62° C. and most preferably at 68° C., in particular for 1 hour in 0.2×SSC buffer and 0.1% SDS at 55° C., preferably at 62° C. and most preferably at 68° C.

The sequences of the invention include fragments of the reference nucleic acid sequence or amino acid sequence. A "fragment" of the hsp70 nucleic acid reference sequence is any part of that sequence comprising at least 50, optionally at least 75, or at least 100 consecutive nucleotides.

A "fragment" of a hsp70 protein is understood to mean any peptide molecule having at least 25, optionally at least 35, or at least 45 contiguous amino acids of the reference hsp70 amino acid sequence. An "immunogenic" protein fragment is one capable of eliciting antibodies that neutralize pathogen infectivity and/or mediate antibody-complement or antibody dependent cell cytotoxicity to provide protection of an immunized host. One example of an immunogenic fragment of *Arthrobacter* hsp70 is the Domain II fragment, analogous to the *Mycobacterium* Domain II fragment (Huang Q et al. (2000) J. Exp. Med. 191(2): 403-8). The Domain II fragment of *Arthrobacter* hsp70 is the sequence from amino acid 162 to 365 of SEQ ID NO:2 or a portion thereof consisting of at least 100 contiguous amino acids, more preferably at least 150 contiguous amino acids, and most preferably at least 200 contiguous amino acids thereof.

The amino acid sequences of the invention also comprise derivatives of the sequence of FIG. 2, or of homologues of that sequence. A "derivative" of an amino acid sequence is a sequence related to the reference sequence either on the amino acid sequence level (e.g. a homologous sequence wherein certain naturally-occurring amino acids are replaced with synthetic amino acid substitutes) or at the 3D level, i.e. molecules having approximately the same shape and conformation as the reference amino acid sequence. Thus, derivatives include mutants, mimetics, mimotopes, analogues, monomeric forms and functional equivalents. Amino acid sequence derivatives retain the ability to induce the production of antibodies that recognize and (cross)-react with the antigens from fish pathogens such as *R. salmoninarum* and *Piscirickettsia salmonis* and/or to induce an immune response in fish that protects against infection with these pathogens.

The hsp70 nucleic acid sequences of the invention incorporate the Open Reading Frame (ORF) of the hsp70 gene, but also the 5' and 3' Untranslated Regions (UTR). The invention includes any component promoter, enhancer, regulatory, terminator and localization elements, and use of these elements in conjunction with heterologous genes. In particular, the invention extends to a DNA expression vector comprising the promoter sequence of *Arthrobacter* hsp70 (as depicted in SEQ ID NO: 1), or a substantially homologous sequence, linked to a heterologous gene, for driving expression of that gene.

The *Arthrobacter* hsp70 sequence listing provided herewith (SEQ ID NO:1) is the sequence of the gene identified by genomic cloning to be present in *Arthrobacter*, and SEQ ID NO:2 is the amino acid sequence inferred therefrom. A culture of the source *Arthrobacter* strain was deposited under Accession No. ATCC 55921 with the American Type Culture Collection (10801 University Boulevard, Manassas, Va. 20110-2209) on 20 Dec. 1996.

The hsp proteins of species of the same genus are generally very highly conserved, so it is to be expected that the sequences of hsp70 genes and proteins native to other *Arthrobacter* species, will not diverge greatly from SEQ ID NO:1 and SEQ ID NO:2, respectively. Therefore the present invention extends also to these related hsp70 molecules. Knowledge of sequence of the hsp70 gene from one Corynebacterial species facilitates isolation of the same genes from related organisms. Procedures for isolation of these genes are well known in the art.

An "isolated" hsp70 gene or nucleic acid sequence is understood to mean the gene or sequence other than in its natural context within the *Arthrobacter* genome. DNA encoding hsp70 may be obtained from a cDNA library prepared from cell matter expressing the hsp70 (hsps are ubiquitous and expressed in abundance). The hsp70 encoding gene may also be obtained from a genomic library, such as by following steps described in Example 1, or by oligonucleotide synthesis.

Native hsp70 proteins can be isolated from bacterial cell sources by an appropriate purification scheme using standard protein purification techniques. The identity of the protein can be confirmed, for instance, by Western blotting or immunoprecipitation using antibodies to *Arthrobacter* ATCC 55921 hsp70 antigen. N-terminal amino acid sequencing of purified protein can be used to determine partial or complete amino acid sequences. This enables design of probes to facilitate isolation of the native hsp70 sequence from a cDNA or genomic library.

Libraries can be screened with probes (such as antibodies to the hsp70 or oligonucleotides of at least about 20-80 bases) designed to identify the gene of interest or the protein encoded by it. For instance, the probes may be designed to be homologous to parts of the *Arthrobacter* gene sequence disclosed herein. Alternatively, the probes may have a high degree of homology with other bacterial hsp genes, such as the *Vibrio* hsp70 gene sequence. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding hsp70 is to use PCR methodology [Sambrook et al., supra; Dieffenbach et al., PCR Primer: A Laboratory Manual (Cold Spring Harbor Laboratory Press, 1995)].

Sequences identified in such library screening methods can be compared and aligned to the hsp70 disclosed in SEQ ID NO:1 or other known hsp sequences deposited and available in public databases such as GenBank. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

The *Arthrobacter* hsp70 protein can be seen to bear a resemblance to homologues in other species, especially bacterial species. It is known that hsp genes are highly conserved between related species. However, it came as a surprise to discover that the *Arthrobacter* hsp70 exhibits near identity to the hsp70 from *Mycobacterium tuberculosis* and *Mycobacterium leprae* in the N-terminal region (the first 20 amino adds are in fact identical).

In the Experiment described in Example 2, an abundant *Arthrobacter* surface protein of about 67 kDa that is apparently linked to cell wall peptidoglycan was analysed by N-terminal amino acid sequencing. The N-terminal amino acid sequence of 20 residues was found to be identical to that of *Mycobacterium* hsp70, and this 67 kDa protein is believed to correspond to the hsp70 protein of the present invention. In one aspect the invention provides an isolated heat shock protein of approximately 67 kDa measured by SDS-PAGE which is localized to the cell wall of *Arthrobacter* cells and has the N-terminal amino acid sequence: (M)SRAVGIDLGTTNSV-VSVLE (SEQ ID NO: 3).

The results of our experiments demonstrate that the immunogenicity of *Arthrobacter* hsp70 in fish is comparable with that of *Mycobacterium* hsp70 in mammals. With the benefit of hindsight, we now believe that *Arthrobacter* hsp70 accounts to some degree for the disease protection conferred by the a live *Arthrobacter* vaccine when used to vaccinate fish.

The present application in fact provides the first evidence that an isolated or purified heat shock protein of any origin is efficacious in a vaccine for fish. The immune system of fish is not directly comparable to that of other species, especially mammals, and is poorly understood. It is therefore surprising that heat shock proteins are capable of inducing a powerful immune response in fish. In one aspect the invention concerns the use of an isolated or purified heat shock protein in the preparation of a vaccine composition for administration to fish. Preferably the heat shock protein is used as an adjuvant for the vaccine composition, or as a carrier for a heterologous molecule in the vaccine composition. The heat shock protein is preferably a member of the hsp70 family, but alternatively can be in any other class of known heat shock proteins, such as hsp60, hsp90, hsp100 or any of the small heat shock proteins (sHSPs). The heat shock protein can be from any species, prokaryotic or eukaryotic, but is preferably from a bacterial species, such as *Arthrobacter*.

The realization that *Arthrobacter* and *Mycobacterium* share highly homologous hsp70 genes opens up many unforeseen applications for the *Arthrobacter* homologue. Isolated *Mycobacterium* hsp70 protein has been demonstrated to perform as an effective vaccine adjuvant. *Arthrobacter* hsp70 can also be used as an adjuvant in pure or isolated form in conjunction with an antigen. An "adjuvant" as defined herein is a substance that nonspecifically augments the specific immune response to an antigen when administered in conjunction with the antigen, or when administered separately into the same site. In one aspect of the invention isolated or purified *Arthrobacter* hsp70 protein is used as an adjuvant for an animal vaccine, especially a vaccine for fish. In a related application, the hsp70 gene or a portion thereof is provided on a DNA vector in order to adjuvant a nucleic acid vaccine. Within the scope of the invention there are provided vaccine compositions comprising the hsp70 amino acid or nucleic acid sequences of the invention in conjunction with at least one other antigen or antigen-encoding nucleic acid sequence, and one or more pharmaceutically acceptable excipients. The other antigen may be a recombinant or isolated single antigen, or it may be a mixture of antigen molecules from a pathogen.

The use of *Arthrobacter* hsp70 as an adjuvant allows doctors and veterinarians to move away from use of the traditional attenuated live *Mycobacterial* adjuvants, which present a risk to the health of animals due to the danger of reversion to the virulent bacterial strain. There is an additional benefit for aquaculture in that injection of *Arthrobacter* hsp70 nucleic acid or isolated protein into fish does not result in disfiguring swellings or nodules at the injection site, which are common with conventional adjuvants and which lower the commercial value of the fish.

*Arthrobacter* hsp70 protein is not only effective in adjuvanting vaccines comprising other antigens, but it also has immunogenic activity in its own right. *Arthrobacter* hsp70 can provide the active principle for a vaccine to prevent or treat a variety of human and veterinary diseases, including diseases caused by fish pathogens, in particular, but not limited to, BKD and SRS (salmonid rickettsial septicaemia). In a further aspect of the invention a vaccine composition comprises isolated or purified hsp70 protein as the sole antigenic or immunogenic component, together with one or more pharmaceutically acceptable excipients. Also provided is a nucleic acid vaccine composition comprising an expression vector comprising a hsp70 nucleic acid sequence of the present invention encoding an antigen being the sole antigenic or immunogenic component of the vaccine composition, together with one or more pharmaceutically acceptable excipients.

The highly immunogenic potential of *Arthrobacter* hsp70 deduced from homology to the *Mycobacterium* and other hsp70 also suggests the possibility of preparing gene or peptide covalent conjugates (e.g. chimeras or fusions) of a hsp70 protein with a heterologous (non-hsp70) molecule, usually, but not limited to, a non-hsp70 protein (e.g. a hapten). In this manner, the *Arthrobacter* hsp70 protein acts as an adjuvant-free carrier to stimulate the humoral and cellular immune responses to the accompanying heterologous molecule. As used herein the term "carrier" refers to a molecule containing T cell epitopes which, when covalently linked to a second molecule, helps to elicit and enhance immune responses against the second molecule (which may be a protein, peptide, oligonucleotide or oligosaccharide).

This approach to vaccine development is particularly advantageous when the antigenic peptide concerned is not very large and poorly immunogenic, yet would be a suitable target for a vaccine. The heterologous molecule carried by the *Arthrobacter* hsp70 is advantageously a protein hapten or a non-protein molecule such as a carbohydrate moiety As used herein, a hsp70 "fusion protein" comprises a hsp70 polypeptide operatively linked to a different polypeptide (a "heterologous polypeptide"). A "heterologous polypeptide" or a "non-hsp70 polypeptide" refers to a polypeptide having an amino acid sequence corresponding to a protein which is not substantially homologous to a hsp70 protein. Within a hsp70 fusion polypeptide can correspond to all or a portion of a hsp70 protein (such as a Domain II portion). Within the fusion protein, the term "operatively linked" indicates that the hsp70 polypeptide and the non-hsp70 polypeptide are fused in-frame to each other. The non-hsp70 polypeptide can be fused to the N-terminus or C-terminus of the hsp70 polypeptide, or can be embedded within the hsp70 polypeptide.

It is possible to link a hsp70 polypeptide and a heterologous molecule by means of a covalent or non-covalent linkage other than by creating a fusion protein. A "heterologous molecule" is any protein, peptide, oligonucleotide or oligosaccharide molecule other than a hsp70 protein. For instance, chemical spacer groups may be inserted between polypeptides, e.g. to create a molecule of general formula hsp70-X-heterologous polypeptide, where X is a spacer group, such as a short sequence of one or more amino acids. Alternatively, the hsp70 polypeptide may be covalently linked other than through amide linkages in a linear chain of amino acids, for instance by chemical conjugation or by chemical, light (e.g. UV)- or radiation-induced crosslinking to the non-hsp molecule. Glutaraldehyde and mercapto-binding linkers are examples of suitable chemical cross-linkers. Specific possibilities are EDC+NHS or sulfo-NHS, sulfo-SMCC, sulfo-SBED, and SAED, which are commercially available in kit form.

In a preferred embodiment of the invention, the hsp70 polypeptide is conjugated to a hapten. A hapten is a substance of low molecular mass (e.g. a peptide or oligosaccharide) that can bind antibodies, but which will induce an immune response only if covalently attached to a large carrier molecule.

It is possible to conjugate hsp70 with entire populations of proteins from antigenic cells or particles by in vitro complexing of cell lysates, fractions, extracts, viral particles, and the like.

The heterologous molecules or polypeptides can be from any source, but are most likely to be components of a pathogenic organism. In particular they may be polypeptides from viral, bacterial, protozoan, helmintic, or fungal pathogens of animals, especially aquatic animals.

The isolated hsp70 gene can be exploited in the conventional manner, by cloning the gene into an expression vector for generation of large quantities of purified or isolated recombinant hsp70 protein (or hsp70 fusion protein). A purified hsp70 antigen can also be obtained by non-recombinant techniques. The protein is abundant and can be extracted from *Arthrobacter* cells by conventional purification methods. Alternatively, the hsp70 protein or polypeptide can be synthesized chemically using standard peptide synthesis techniques. A vaccine comprising this purified or isolated recombinant or non-recombinant protein can be termed an antigen-based vaccine.

An "isolated" or "purified" protein is defined as being substantially free of cellular material or other contaminating proteins from the cell or tissue source from which the hsp70 protein is derived, or substantially free from chemical precursors or other chemicals when chemically synthesized. The language "substantially free of cellular material" includes preparations of hsp70 protein in which the protein is separated from cellular components of the cells from which it is isolated or recombinantly produced. In one embodiment, the language "substantially free of cellular material" includes preparations of hsp70 protein having less than about 30% (by dry weight) of non-hsp70 protein (also referred to herein as a "contaminating protein"), more preferably less than about 20% of non-hsp70 protein, still more preferably less than about 10% of non-hsp70 protein, and most preferably less than about 5% non-hsp70 protein. When the hsp70 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

A hsp70 "enriched" *Arthrobacter* cell extract may also be used in performance of the invention as an alternative to isolated or purified hsp70. An "enriched" cell extract can be obtained by inactivating or killing whole *Arthrobacter* cells, lysing the cells, fractionating the resulting cell lysate by conventional means, and identifying fractions in which hsp70 protein is more abundant compared with other fractions (for instance by Western blotting). A hsp70 enriched cell extract can also be prepared by cultivating *Arthrobacter* cells under conditions which result in elevated expression of heat shock proteins (i.e. under heat or other cellular stress conditions), and inactivating or killing, and lysing the cells. Optionally the resulting cell extract (lysate) is fractionated and hsp70-rich fractions are identified.

Preferably, a hsp70 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, eds. Ausubel et al. John Wiley & Sons: 1992).

Another aspect of the invention pertains to vectors, preferably expression vectors, comprising a nucleic acid sequencing encoding hsp70 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of directing the expression of genes to which they are operatively linked. Such vectors are referred to herein as "expression vectors". In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, operatively linked to the nucleic acid sequence to be expressed. Expression vectors of the invention may be used for expression within the intended recipient of the hsp70 antigen (as a DNA vaccine) or for expression within a host organism other than the final recipient (for production of recombinant antigen vaccines).

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. hsp70 proteins, mutant forms of hsp70, fusion proteins of hsp70 with a heterologous peptide, etc.).

Another aspect of the invention pertains to host cells into which a recombinant expression vector of the invention has been introduced by transformation. A host cell can be any prokaryotic or eukaryotic cell (including a eukaryotic cell within a multicellular eukaryotic organism). For example, hsp proteins can be expressed in bacterial cells such as *E. coli*, insect cells (using baculovirus expression vectors), yeast cells or mammalian cells. Other suitable host cells are known to those skilled in the art (e.g. Goeddel, supra). The recombinant expression vector may be designed to be expressed in a host fish cell (following DNA vaccination). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

The hsp70 gene can be incorporated into a Nucleic Acid Vaccine (NAV), whereby the NAV is taken up by host cells of a living animal, and expression of the hsp70 gene takes place within the cytosol. Because short peptides of intracellular hsp70 antigens are transported to the cell surface where they can make contact with the MHC I system, NAV-originating hsp70 antigens are ideally positioned for inducing a cellular immune response.

A hsp70 gene inserted into a DNA vector can be inoculated directly into a fish (e.g. orally, intramuscularly or intraperitoneally) for expression in vivo within fish cells. DNA vaccination can also be carried out in other animal species. Thus, in one aspect of the invention there is provided a nucleic acid vaccine comprising a pharmaceutically acceptable carrier and a DNA plasmid in which a nucleic acid sequence encoding *Arthrobacter* hsp70 is operably linked to a transcriptional regulatory sequence. Transcriptional regulatory sequences include promoters, polyadenylation sequences and other nucleotide sequences such as the immune-stimulating oligonucleotides having unmethylated CpG dinucleotides, or nucleotide sequences that code for other antigenic proteins or adjuvanting cytokines. The presence of eukaryotic or viral transcriptional regulatory sequence(s) allows expression of the hsp70 gene in fish cells. The DNA plasmid itself can be replicated in bacterial cells in order to prepare a vaccine composition, but generally lacks transcriptional regulatory sequences permitting hsp70 gene expression within prokaryotic cells. For optimal in vivo expression it may be preferred to select transcriptional regulatory sequences endogenous to the fish to be vaccinated. For instance, endogenous cytokine or actin gene promoters may be considered. The DNA can be present in naked form or it can be administered together with an agent facilitating cellular uptake (e.g. liposomes or cationic lipids). The technology of DNA vaccination of fish is explained in more detail in U.S. Pat. No. 5,780,448, which is incorporated herein by reference.

The present invention also relates to a method of generating monoclonal or polyclonal antibodies to a molecule using a conjugate of a hsp70 protein joined to the molecule. In this embodiment, an effective amount of the conjugate (i.e., an amount which results in an immune response in the host) is introduced into an animal host which results in production of antibodies to the substance in the host. The antibodies are removed from the host and purified using known techniques (e.g. chromatography), thereby resulting in production of polyclonal antibodies. Alternatively, the antibodies produced using the method of the present invention can be used to generate hybridoma cells which produce monoclonal antibodies using known techniques.

In one embodiment of the invention the promoter sequence of the *Arthrobacter* hsp70 gene is used to drive expression of a heterologous gene, i.e. a gene other than the gene encoding *Arthrobacter* hsp70. The promoter can be inserted upstream of a heterologous gene in the chromosomal DNA of an organism, or into an extrachromosomal plasmid or other expression vector. For instance, in the event that it is desired to overexpress an endogenous *Arthrobacter* gene, or to insert a foreign gene into an endogenous plasmid of *Arthrobacter*, an upstream hsp70 promoter can drive expression of that heterologous gene in response to a stimulus such as heat shock.

The vaccines manufactured in accordance with the methodology of the invention are suited for administering to any species of animal having a humoral and/or cellular immune system. Humans are included within the meaning of "animal" and "mammal" in the present context. *Arthrobacter* hsp70 can be employed to adjuvant any vaccine for mammals, birds, reptiles or fish (finfish or shellfish). Similarly, *Arthrobacter* hsp70 can be used in vaccines as carriers for covalently-attached antigens, optionally to the exclusion of any conventional adjuvant (so-called "non-adjuvant" vaccines). *Arthrobacter* hsp70 is also capable of being used as an immunogen (optionally as the sole immunogen) in a vaccine for raising an immune response against specific diseases, notably BKD, Salmonid Rickettsial Septicemia (SRS), and other infectious diseases in fish.

The term "vaccine" is used in the broad sense, and includes not only compositions to be used for immunization against pathogens, but also anti-tumor vaccines, vaccines based on autogenous antigens (e.g. for chemical castration), and so on. Within the sphere of veterinary vaccination, any non-human animal can be vaccinated, including the major species of farmed land animals, namely cattle, horses, sheep, swine and poultry birds. For aquaculture, the vaccines of the invention can be employed in shellfish or in finfish, especially for treatment of teleosts such as salmon, trout, carp, sea bream, sea bass, yellowtail, catfish, halibut, haddock, or optionally for treatment of other aquatic species such as crustaceans (e.g. shrimps, prawns, lobster, crabs) and mollusks (e.g. oysters, mussels). There are no limits to the candidate antigens suitable for combining with *Arthrobacter* hsp70 sequences in a vaccine. Pathogenic antigens can be derived from bacteria, viruses, protozoa, nematodes and fungi. One particular focus is on antigens, particularly surface antigens, of fish pathogenic organisms.

Hsp70 amino acid or nucleic acid sequences can be used in vaccine compositions in conjunction with, or conjugated to, bacterial, protozoan, viral or fungal antigens from diseases affecting shellfish or finfish, including antigens (or their coding sequences) derived from: Infectious Salmon Anaemia Virus (ISAV), Infectious Pancreatic Necrosis Virus (IPNV), Infectious Hematopoietic Necrosis Virus (IHNV), Iridovirus, Nervous Necrosis Virus (NNV), Salmon Pancreas Disease Virus (SPDV), Spring Viremia of Carp Virus (SVCV), Viral Hemorrhagic Septicemia Virus (VHSV), Yellow-head virus (YHV), Taura Syndrome Virus (TSV), White Spot Syndrome Virus (WSSV), *Renibacterium salmoninarum* (causative agent of Bacterial Kidney Disease), *Piscirickettsia salmonis* (causative agent of Salmonid Rickettsial Septicemia), *Vibrio* spp, *Aeromonas* spp, *Yersinia ruckerii, Pseudomonas* spp, *Photobacterium damselae*, etc. A large and growing number of polypeptides from these and other pathogenic organisms have been purified and/or cloned and expressed and are available to be conjugated to, or provided in conjunction with, *Arthrobacter* hsp70 or its coding sequence in a vaccine composition. Preferred examples include IPNV proteins VP1, VP2, VP3 and NS and their coding nucleotide sequences; ISAV proteins disclosed in WO 01/10469 including hemagglutinin, nucleocapsid, polymerase and segment 7 P4 and P5 proteins, and their coding nucleotide sequences: *P. salmonis* proteins disclosed in WO 01/68865 including OspA and IcmE and their coding nucleotide sequences; nodavirus proteins such as the nucleocapsid; and structural polypeptides from SPDV and their coding nucleotide sequences (disclosed in WO 99/58639). A preferred vaccine composition according to the invention comprises a DNA expression vector carrying the hsp70 nucleotide sequence fused in-frame with the IPNV VP2 sequence or the IPNV VP3 sequence. Optionally, the vaccine comprises a first plasmid carrying the hsp70-VP2 fusion and a second plasmid carrying the hsp70-VP3 fusion.

Hsp70 sequences can also be used in conjunction with, or conjugated to, antigens (or their coding sequences) from other animal pathogens and parasites, including: Bovine Viral Diarrhea Virus (BVDV), Bovine Herpesvirus (BHV), Foot and mouth disease virus, Bovine Respiratory Syncytial Virus (BRSV), Parainfluenza type 3 virus (PI3), infectious Bovine Rhinotracheitis (IBR), Porcine Respiratory and Reproductive Syndrome Virus (PRRSV), *Mycobacteria, Leishmania, Ehrlichia, Eimeria, Clostridia, Pasteurella, Mycoplasma* (e.g. *M. bovis, M. hyopneumoniae*) *Leptospira, Brachyspira, Salmonella, Brucella, Neospora, Cryptosporidium, Fusobacterium, E. coli, Rotavirus, Coronavirus, Mannheimia haemolytica, Haemophilus somnus, Actinobacillus pleuropneumoniae, Trypanosoma, Anaplasma, Treponema*, etc.

The invention encompasses the use of hsp70 sequences in conjunction with any of the above-mentioned antigens or their coding sequences in the manufacture of a pharmaceutical composition for the treatment or prevention of disease caused by infection with the disease agent from which the antigen is derived.

The vaccine antigens provided in conjunction with hsp70 gene or protein may be chemically conjugated to the hsp70 (in a chimera or fusion protein) or they may be provided as separate molecules together in a single vaccine composition. As another option, hsp70 gene or protein may be provided with an antigen or antigen-encoding nucleic acid sequence in a kit for separate, sequential or simultaneous administration. The vaccine antigens provided in conjunction with hsp70 gene or protein can be bacterins, cell extracts, recombinant proteins, plasmid-borne genes, or live/attenuated pathogen strains.

It is possible to immunize a subject with the neutral or the salt forms of the present fusion proteins or isolated hsp70 protein, either administered alone or in admixture with a pharmaceutically acceptable vehicle or excipient. Typically, vaccines are prepared as liquid solutions or suspensions; solid forms suitable for solution in, or suspension in, liquid vehicles prior to administration may also be prepared. The preparation may be emulsified or the active ingredient encapsulated in liposome vehicles. The pharmaceutical compositions of the invention may be administered in a form for immediate release or by extended release.

Pharmaceutically acceptable vehicles are, for example, water, saline, dextrose, glycerol, auxiliary substances such as wetting or emulsifying agents, bulking agents, binders, disintegrants, diluents, lubricants, pH buffering agents, or conventional adjuvants such as muramyl dipeptides, avridine, aluminium hydroxide, oils, saponins, block co-polymers and other substances known in the art.

To immunize a subject, a hsp70 antigen or hsp70 gene vector can be administered parenterally, usually by intramuscular injection in an appropriate vehicle, but optionally by the subcutaneous route, by intravenous injection or by intradermal or intranasal delivery. In the case of immunization of fish, the typical routes of administration are by injection into the peritoneal cavity, orally in feed, or by immersion. The preferred antigenic vaccine compositions of the invention are in a form suitable for administration by injection or immersion. DNA vaccination is generally by intramuscular injection.

The effective dosage may vary depending on the size and species of the subject, and according to the mode of administration. The optimal dosage can be determined through trial and error by a doctor or veterinarian. Typically, a single dose of hsp70 antigen will be in the range of from about 0.01 to 1000 μg per kg body weight, preferably 0.5 to 500 μg per kg, more preferably 0.1 to 100 μg per kg. For DNA vaccines, a minimum dosage of 10 pg up to dosages of 1000 μg of plasmid per animal should be sufficient for suitable expression of the antigen in vivo.

The novel antigens disclosed as part of the present invention are also useful in screening for antibodies to pathogenic proteins. The invention additionally includes diagnostic uses of these antigens, for instance in the preparation of a diagnostic kit, useful for testing animals for the presence of disease-causing organisms.

Antibodies raised against the purified hsp70 antigen and/or hsp70 fusion proteins as disclosed herein are also comprised within the invention. It is contemplated that such antibodies could have both diagnostic and therapeutic applications in disease management and fish health. Both polyclonal antibodies and monoclonal antibodies may be useful in this respect. Procedures for immunizing animals, eg. mice, with proteins and selection of hybridomas producing immunogen-specific monoclonal antibodies are well know in the art (see for example Kohler and Milstein (1975) Nature 256: 495-497). Sandwich assays and ELISA may be mentioned as specific examples of diagnostic assays.

The hsp70 nucleic acid sequence of the invention has diagnostics applications, for instance in the design of primers for PCR amplification assays.

EXAMPLES

Example 1

Isolation and Sequencing of hsp70 Gene from the Genome of *Arthrobacter* ATCC 55921

A 5 ml culture of *Arthrobacter* is grown overnight shaking at 30° C. in LB containing kanamycin (30 μg/ml). DNA extraction is then carried out using the Puregene DNA isolation kit (Gentra) or Instagene™ Resin according to the manufacturer's instructions.

Degenerate PCR

Areas of greatest similarity between several mycobacterial and streptomyces hsp70 (dnaK) sequences at the nucleotide level are used to design degenerate primers for PCR and sequencing. The selected primers are dnak-1Fdeg (5'-gtcgg-natcgacctvggnac-3') (SEQ ID NO: 4) and dnak-4Rdeg (5'-gcggtsggctcgttgac-3') (SEQ ID NO: 5). These primers are used for amplification of *Arthrobacter* DNA in a PCR reaction with a 50° C. annealing temperature. The quality of the amplified DNA is assessed by gel electrophoresis. A 10 μl aliquot is electrophoresed on a 0.8% agarose gel in 1× Tris-borate electrophoresis buffer (TBE) at 100V for about 1 hour. The 650 bp product is then excised from the gel and purified using the Qiaquick purification kit (Qiagen). The PCR product is cleaned using Qiagen PCR clean up kit according to the manufacturer's instructions) and sequenced according to the manufacturer's instructions using BigDye primer chemistry (Applied Biosystems) and each of the primers used for the PCR. The extension reaction mixtures are prepared using the ABI PRISM (8r) BigDye Terminator Cycle Sequencing Ready Reaction mix, ~600 ng of DNA template, 3.2 pmol of the appropriate primer and ddH$_2$O to 20 μl. Conditions for cycle sequencing are as follows: the thermal cycler is set to 25 cycles consisting of 96° C. for 10 s, 50° C. for 5 s, and 60° C. for 4 mm. The sequence shows this fragment to contain the first approx. 400 bp of the dnaK gene.

In order to obtain additional hsp70/dnaK gene sequence, degenerate primers are used to amplify a downstream portion of the *Arthrobacter* hsp70 gene. These are selected from Galley et al. (1992) Biochemica et Biophysica Acta 1130: 203-208. [Forward primer hsp70 universal-F1 (5' CAR GCN CAN AAR GAY GCN GG 3') (SEQ ID NO: 6), Reverse primer hsp70 universal-R1: (5' GCN CAN GCY TCR TCN GGR TT 3') (SEQ ID NO: 7)]. The primers are designed to anneal to two highly conserved regions within the hsp70 gene to generate a 650 bp product.

The PCR reaction consists of (in 50 μl total volume): 5 μl 10× PCR buffer, 5 μl 25 mM MgCl$_2$, 2.5 μl 10 mM each dNTPs, 2 μl Hsp70 universal-F1 (200 μM), 2 μl Hsp70 universal-R1 (200 μM), 0.5 μl Amplitaq DNA polymerase (5 U/μl), 10 μl of instagene extracted DNA, 23 μl ddH$_2$O. The PCR reaction is cycled as follows: 2 min at 94° C., then 40 PCR cycles consisting of: 1.0 min at 94° C., 0.5 min at either 50° C. or 58° C., and 1.0 min at 72° C. PCR cycling is completed with a 3.0 min elongation step at 72° C. The PCR product is electrophoresed, cleaned and sequenced as described above. The sequence of this fragment is found to overlap and extend 3' of the ~400 bp sequence identified in the first sequencing attempt.

Genome Walking

Genome walking is used to extend the sequence 5' and 3' of the already identified sequences. Primers are designed from the sequences described in the Genome Walker manual (Clontech). Initially, four genomic libraries are made (DraI, EcoRV, PvuII, StuI), and subsequently three additional libraries are made (AluI, ScaI, and SnaF1). All libraries and the subsequent PCR reactions are as described in the Genome Walker manual.

5' Genome walking produces a ~500 bp fragment which overlaps with the sequence previously obtained. The 5' extension contains the start codon and the 5' UTR of the hsp70 gene. 3' walking fails to extend the gene.

RACE

3' RACE is used to obtain additional 3' sequence. RNA is isolated from an overnight culture of *Arthrobacter* (cultured as above) using the Purescript (Gentra) RNA isolation kit according to the manufacturer's instructions. 3' RACE is performed using the Boehringer Mannheim 5'3' RACE kit according to manufacturer's instructions. Primers for RACE are designed from the 3' end of the known sequence. The PCR reaction is performed as described except that it contains 10% DMSO and has a 55° C. annealing temperature. A band of ~1.0 kb is amplified and cloned into a pCR4 vector using invitrogen's TOPO sequencing kit according to the accompanying protocol. Colonies are screened using vector primers and selected clones are grown overnight, then DNA extractions are carried out using invitrogen's SNAP miniprep kit and sequenced using vector primers as described above.

Contigs are assembled using Genecode's Sequencher software. A Genbank search using the contigged sequences confirms it is hsp70.

The remainder of the hsp70 gene and 3'UTR are obtained by genome walking as described above. Again, contigs are identified using Genecode's Sequencher software. A Genbank search using the contigged sequences confirms it includes the hsp70 gene including 3' UTR and 5' UTR.

Example 2

Characterization of *Arthrobacter* Cell Wall Proteins

Electrophoresis and Western Blotting

*Arthrobacter* ATCC 55921 cell suspensions are prepared by removing subcultured bacteria directly from tryptic soy agar (TSA) plates following incubation for 48 hours at 23° C. Bacteria are resuspended in 10 ml of "TET" buffer consisting of 100 mM Tris-HCl buffer of pH 7.2, 1 mM EDTA and 0.1% Triton-X 100 (BioRad Laboratories, Hercules, Calif.), to an optical density of approximately 50 OD660 units (where 1 OD600 has been estimated to be $1 \times 10^9$ cells), and centrifuged at 6500 g. The supernatant is discarded and the cells are suspended in a further 10 ml of TET and the centrifugation step is repeated. The cell pellet is resuspended in 4 ml of TET and separated as 1 ml aliquots into 1.5 ml microtubes. One of the aliquots is further mixed with 200 µl of 5 mg ml$^{-1}$ chicken egg white lysozyme and incubated with shaking overnight (18 h) at 37° C. The cell suspension is centrifuged at maximum speed for 5 min in a bench top microcentrifuge. 150 µl of cell free supernatant is mixed with 50 µl of NuPage 4×LDS samples buffer (Invitrogen Carlsbad, Calif.) and incubated at 70° C. for 10 min with shaking. 10 µl aliquots of the resulting supernatant are analysed on 8% Mini Protean II gels (Biorad) and Western blotted to PVDF (Millipore, Bedford Mass.) with a semi-dry transfer unit (BioRad) for 30 min at 20V. Immediately after blotting, membranes are washed in 0.1% Ponceau S (Amersham Pharmacia Biotech, Uppsala, Sweden) for 1 min and destained with several washes of distilled water until blotted proteins were visible. Molecular weight standards and certain proteins are marked with pencil for reference points following immunostaining before removal of pink coloration by repeated washes in distilled water and air drying the membrane in preparation for further staining.

For Coomassie blue identification of protein bands for amino acid sequencing the decolorized membranes are incubated in a solution containing 50% methanol, 7% acetic acid, and 0.1% of R-250 for 10 min followed by destaining of background using the aforementioned solution without Coomassie blue. The blot is subsequently rinsed in distilled deionised water for 10 minutes and air dried for N-terminal amino acid sequencing by Edman degradation using an automated protein sequencer (Applied Biosystems).

Development of immunoreactive antigens is achieved by incubation of the dried blot with a 1 in 200 dilution of antibody (polyclonal rabbit anti-*Arthrobacter*) in 1% casein trisbuffered saline pH 7.4 (cTBS) (BioRad) for 60 min, 2 washes of 10 sec with TBS followed by incubation with 1:2000 dilution of goat anti-rabbit immunoglobulin alkaline phosphatase (Pierce, Rockford Ill.). Colour development is achieved with 1-Step NBT/BCIP (Pierce) for approximately 3 min and terminated by washing in distilled water. All incubations are carried out in a final volume of 10 ml on a red rocker platform (Hoefer, San Francisco, Calif.). Documentation is achieved with an Imagemaster and associated software (Amersham Pharmacia Biotech, Uppsala Sweden). Estimation of molecular weights is achieved through comparison of migration of antigens with Precision broad range prestained standards (BioRad). Estimation of molecular weight is achieved by calculation of relative mobility using First Order Lagrange.

Antiserum Production

Polyclonal antiserum to *Arthobacter* antigens is produced by i.m. injection of a New Zealand rabbit with 0.5 ml of a suspension consisting of 3 parts $4 \times 10^8$ cells previously washed in sterile Dulbecco's saline and 1 part Freund's incomplete adjuvant. After 4 weeks the same volume of material is injected into the rabbit. 5 ml of blood is harvested from the peripheral ear vein at 6 weeks and serum collected by allowing blood to clot followed by centrifugation.

Results

SDS-PAGE analysis of the lysozyme treated suspensions of *Arthrobacter* reveals the presence of a range of protein bands between 150 and 10 kDa. Preeminent among these are major proteins of approximately 67, 63 and 59 kDa. The 67 kDa protein is apparently cross-linked to the peptidoglycan of the *Arthrobacter* cell wall, because it is only released following treatment with lysozyme.

When the SOS-PAGE protein profiles are Western blotted and stained with an antiserum to whole cells of *Arthrobacter* major immunoreactive bands are identified at 122 and 67 kDa. The N-terminus of the 67 kDa protein is sequenced and found to be SRAVG IDLGT TNSW SVLE. A homology search using the BLAST protein-protein algorithm identifies that the sequence has 100% homology to the hsp70 protein of *Mycobacterium tuberculosis*. This 67 kDa protein is believed to be the same as the hsp70 protein identified by genomic sequencing and disclosed herein.

Example 3

Recombinant Expression of hsp70

The complete coding sequence of *Arthrobacter* heat-shock protein 70 is cloned into the pET30EKLIC vector (Novagen) as a non-fusion and as a fusion peptide. The N-fusion tag consists of 55 amino acids which includes various features to allow further purification of the target protein (included are His tag, S-tag, enterokinase cleavage site). A 200 amino acid active motif located within the HSP70 protein, known as Domain II, is also cloned as a non-fusion and fusion peptide.

Expression of recombinant HSP70 and recombinant Domain II is performed in *E. coli* DE3 cells. Once a suitable cell density is obtained, the DE3 cultures are divided into two separate flasks. Protein expression is induced in one of the cultures with the IPTG substrate while the second serves as a control. Both HSP70 and Domain II, expressed as fusion or non-fusion, are principally found in a soluble form in the cytoplasm or associated with the periplasm of *E. coli*. Thus, in *E. coli* the recombinant HSP70 and Domain II thereof are successfully targeted to the cell surface, just like the native protein in *Arthrobacter*. Inclusion of the fusion tag at the N terminus of the proteins does not appear to affect translocation of the protein. Based on these observations both full length HSP70 and Domain II are capable of translocating other antigenic sequences to the cell surface.

Example 4

Nucleic Acid Vaccine Against IPNV Based on Gene Fusions with hsp70

Atlantic salmon (*Salmo salar*) pre-smolts (35-40 g) maintained in flow through fresh water are anaesthetized with benzocaine diluted in clean aquarium water. Prior to vaccination 6 fish are euthanized by lethal overdose of anaesthetic and bled from the caudal vein for pre-immune serum.

The nucleic acid vaccines and PBS control are vaccinated intramuscularly into the left dorsal flank, just below the dorsal fin, with 50 µl of vaccine. Forty fish are vaccinated per replicate (80 per group, divided between two tanks). Following vaccination fish are allowed to recover in fresh water and allocated to their appropriate tank.

The nucleic acid vaccines undergoing testing are: pUKrsxHSP70-ipnVP2 and pUKrsxHSP70-ipnVP3. These plasmids carry, under the control of a CMV promoter, an in-frame fusion of the complete coding sequences of *Arthrobacter* hsp70 and IPNV VP2 or IPNV VP3, respectively. pUKrsxHSP70-ipnVP2 is tested alone, and both plasmids are also tested together.

For comparison, plasmids are also prepared comprising IPN VP2 protein fused 3' of a sequence known from previous studies to boost the immunoprotective efficacy of the VP2 component by about 20% (i.e. a "gold standard" VP2-based IPNV nucleic acid vaccine).

6 weeks post vaccination the fish are transferred to seawater. On the day prior to challenge serum is samples from 4 fish per replicate group. A sample of muscle from the injection site is also taken and formalin fixed to look for vaccine presence. On day 21 post challenge, serum is sampled from a maximum of 4 surviving fish per replicate group. Following challenge, mortalities are removed daily on first observation and kidneys samples and frozen for analysis by ELISA.

Challenge takes place 4-6 weeks after seawater transfer, by cohabitation with marked sibling fish which have been challenged by intraperitoneal injection of virulent IPNV ($10^6$ cfu). The trial is terminated after 20 weeks.

The results indicate that all of the nucleic acid vaccines based on the VP2 sequence of IPNV are protective against challenge by the virus, including the hsp70-VP2 fusion.

Example 5

Recombinant Hsp70 in a Vaccine Against ISAV

Atlantic salmon parr are acclimated to 0.5 m holding tanks supplied with aerated flowing well water (10° C.) for a week prior to the start of the experiment and fed daily throughout the entire experiment. Each group of 55 fish is split into 2 tanks of 25 to provide for replicate treatment groups. Atlantic salmon parr experience between 60 and 80% mortality when challenged with ISAV.

The fish are anaesthetized and then vaccinated by intraperitoneal injection with 0.2 ml saline, or 0.2 ml saline containing the specific recombinant proteins. The negative control is a PBS injection (saline). The treatment groups are: (A) His-tagged purified *Arthrobacter* hsp70 recombinant protein, 12 μg; (B) ISAV recombinant His-tagged nucleocapsid protein (NC), 12 μg; (C) His-tagged purified *Arthrobacter* hsp70 recombinant protein, 12 μg, admixture with His-tagged ISAV NC, 12 μg; (D) His-tagged purified *Arthrobacter* hsp70 recombinant protein, 12 μg, crosslinked to His-tagged ISAV NC, 12 μg; (E) His-tagged purified *Arthrobacter* hsp70 Domain 2 recombinant protein, 12 μg, admixture with His-tagged ISAV NC, 12 μg; (F) His-tagged purified *Arthrobacter* hsp70 Domain 2 recombinant protein, 12 μg, crosslinked to His-tagged ISAV NC, 12 μg.

Treatment groups D and F receive covalently crosslinked proteins. EDC and sulfo-NHS are used as crosslinking agents, and employed according to standard protocols.

A cohabitation challenge is used, in which a small number of salmon are given an i.p. injection with 0.1 ml cultured virulent ISAV (~$10^4$ $TCID_{50}$ per fish) and added to each tank of treated fish. Mortalities in each tank are monitored daily.

The relative percentage survival is assessed by comparing mortalities between the different treatment groups and controls at specific time-points.

The invention claimed is:

1. An isolated nucleic acid sequence comprising: (a) the nucleic acid sequence of SEQ ID NO:1, or a fully complementary sequence thereof; (b) a nucleotide sequence which encodes amino acid residues 162 to 365 of SEQ ID NO:2, or a fully complementary sequence thereof; (c) nucleotides 291-2153 of SEQ ID NO:1, or a fully complementary sequence thereof; or (d) a nucleotide sequence, or a fully complementary sequence thereof, which under stringent conditions hybridizes with the sequence of SEQ ID NO:1 or its complement, wherein the stringent condition comprises washing for 1 hour at 55° C. with 1×SSC and 0.1% SDS.

2. The isolated nucleic acid sequence of claim 1 fused in-frame to a heterologous coding sequence.

3. The isolated nucleic acid sequence according to claim 2, wherein said heterologous coding sequence encodes an antigen from a source selected from the group consisting of bacteria, virus, fungus, protozoa, nematode, and tumor.

4. A DNA expression Vector comprising the nucleic acid sequence of claim 1, wherein said nucleic acid sequence is operably linked to a transcriptional regulatory sequence.

5. An isolated host cell transformed with the DNA expression vector of claim 4.

6. An isolated nucleic acid molecule, comprising a nucleic acid sequence encoding SEQ ID NO:2, or its fully complementary sequence thereof.

7. A composition comprising the DNA expression vector of claim 4 and a pharmaceutically acceptable carrier.

* * * * *